United States Patent
Ripper et al.

(10) Patent No.: US 8,313,518 B2
(45) Date of Patent: *Nov. 20, 2012

(54) SKIN THERAPY SYSTEM

(75) Inventors: John Ripper, Portland, OR (US); Jason Sagen, Portland, OR (US); Forrest Seitz, Portland, OR (US); Allen Siefken, Portland, OR (US); Stevan Wittenbrock, Portland, OR (US)

(73) Assignee: Oregon Aesthetic Technologies, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/019,193

(22) Filed: Feb. 1, 2011

(65) Prior Publication Data
US 2011/0125231 A1 May 26, 2011

Related U.S. Application Data

(63) Continuation of application No. 11/971,166, filed on Jan. 8, 2008, now Pat. No. 7,896,908.

(51) Int. Cl.
*A61N 5/06* (2006.01)
(52) U.S. Cl. .................. 607/88; 607/90; 606/9
(58) Field of Classification Search ... 606/9; 607/88–94
See application file for complete search history.

(56) References Cited

U.S. PATENT DOCUMENTS

| | | |
|---|---|---|
| 5,931,566 A | 8/1999 | Fraizer |
| 5,989,283 A | 11/1999 | Wilkens |
| 6,016,038 A | 1/2000 | Mueller |
| 6,119,038 A | 9/2000 | Cook |
| 6,183,100 B1 | 2/2001 | Suckow et al. |
| 6,273,884 B1 | 8/2001 | Altshuler et al. |
| 6,340,868 B1 | 1/2002 | Lys et al. |
| 6,443,978 B1 | 9/2002 | Zharov |
| 6,471,716 B1 | 10/2002 | Pecukonis |
| 6,602,275 B1 | 8/2003 | Sullivan |
| D481,463 S | 10/2003 | Cook et al. |
| 6,676,654 B1 | 1/2004 | Balle-Petersen |
| 6,682,204 B2 * | 1/2004 | Mullally et al. .............. 362/235 |
| D490,528 S | 5/2004 | Cook et al. |
| 6,784,357 B1 | 8/2004 | Wang |
| 6,791,283 B2 | 9/2004 | Bowman |

(Continued)

FOREIGN PATENT DOCUMENTS

GB 2390022 12/2003

(Continued)

OTHER PUBLICATIONS

United States Patent and Trademark Office; USPTO Search Authority; PCT US09/030146; International Search Report; Feb. 25, 2009; 1 Page.

(Continued)

*Primary Examiner* — Gregory A Morse
*Assistant Examiner* — Jeffrey Lipitz
(74) *Attorney, Agent, or Firm* — Stolowitz Ford Cowger LLP

(57) ABSTRACT

A light therapy appliance comprises an electronic circuit including Light Emitting Diodes (LEDs) configured to emit light at one or more different wavelengths. A hand held enclosure containing the electronic circuit includes a front lens that directs the multiple different colored lights to a top surface of skin. The light therapy appliance can be programmed for different skin conditions and may be used in conjunction with different topical ointments.

19 Claims, 11 Drawing Sheets

U.S. PATENT DOCUMENTS

| | | | |
|---|---|---|---|
| 6,887,260 | B1 | 5/2005 | McDaniel |
| D538,940 | S | 3/2007 | Balduchini |
| D552,747 | S | 10/2007 | Chang |
| D569,987 | S | 5/2008 | Oberreiter et al. |
| D579,572 | S | 10/2008 | Wittenbrock |
| 7,896,908 | B2 | 3/2011 | Ripper |
| 2002/0029071 | A1 | 3/2002 | Whitehurst |
| 2003/0179584 | A1* | 9/2003 | Pond et al. ............ 362/487 |
| 2003/0206416 | A1 | 11/2003 | Mullally |
| 2004/0093042 | A1* | 5/2004 | Altshuler et al. ......... 607/88 |
| 2004/0101503 | A1 | 5/2004 | Mahe |
| 2004/0124487 | A1* | 7/2004 | Loh ..................... 257/433 |
| 2004/0162549 | A1 | 8/2004 | Altshuler |
| 2004/0167497 | A1 | 8/2004 | Walneck et al. |
| 2004/0167500 | A1 | 8/2004 | Weckwerth et al. |
| 2005/0055070 | A1* | 3/2005 | Jones et al. ............. 607/88 |
| 2005/0080465 | A1 | 4/2005 | Zelickson et al. |
| 2005/0182460 | A1 | 8/2005 | Kent et al. |
| 2005/0187597 | A1 | 8/2005 | Vanderschuit |
| 2005/0192650 | A1 | 9/2005 | Martel |
| 2006/0122668 | A1* | 6/2006 | Anderson et al. ......... 607/88 |
| 2006/0142750 | A1 | 6/2006 | DaSilva |
| 2006/0224217 | A1 | 10/2006 | Burgmann |
| 2007/0038206 | A1 | 2/2007 | Altshuler et al. |
| 2007/0159818 | A1 | 7/2007 | Rueggeberg |
| 2007/0185553 | A1 | 8/2007 | Kennedy |
| 2008/0014011 | A1 | 1/2008 | Rossen |
| 2008/0131836 | A1 | 6/2008 | Rueggeberg |
| 2008/0208297 | A1* | 8/2008 | Gertner et al. ............ 607/92 |
| 2009/0177253 | A1 | 7/2009 | Darm |

FOREIGN PATENT DOCUMENTS

| | | |
|---|---|---|
| WO | 2009089177 | 7/2009 |

OTHER PUBLICATIONS

Papageorgiou P. et al.; Phototherapy with blue (415) nm and red (660 nm)light in the treatment of acne vulgaris; 2000; British Journal of Dermatology, 142; 973-978.

International Bureau of WIPO; PCT/US2009/030146 International Preliminary Report on Patentability and Written Opinion; Jul. 13, 2010; 9 Pages.

Stolowitz Ford Cowger LLP; Related Case Listing; Jan. 31, 2011; 1 Page.

EPO; Extended Search Report; EP 09700242; Dec. 16, 2010; 6 pages.

Stolowitz Ford Cowger LLP; Related Case Listing; May 21, 2012.

* cited by examiner

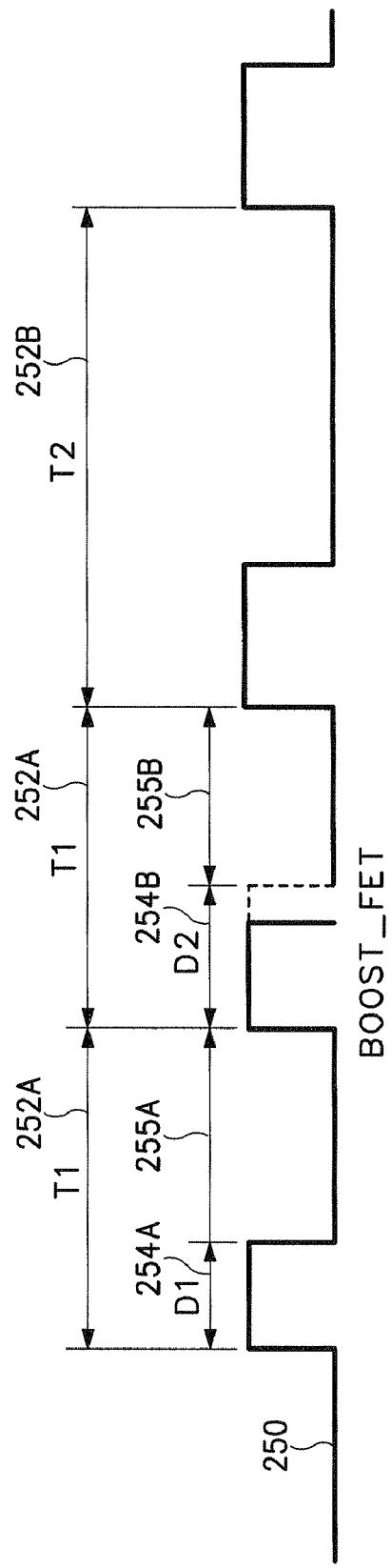

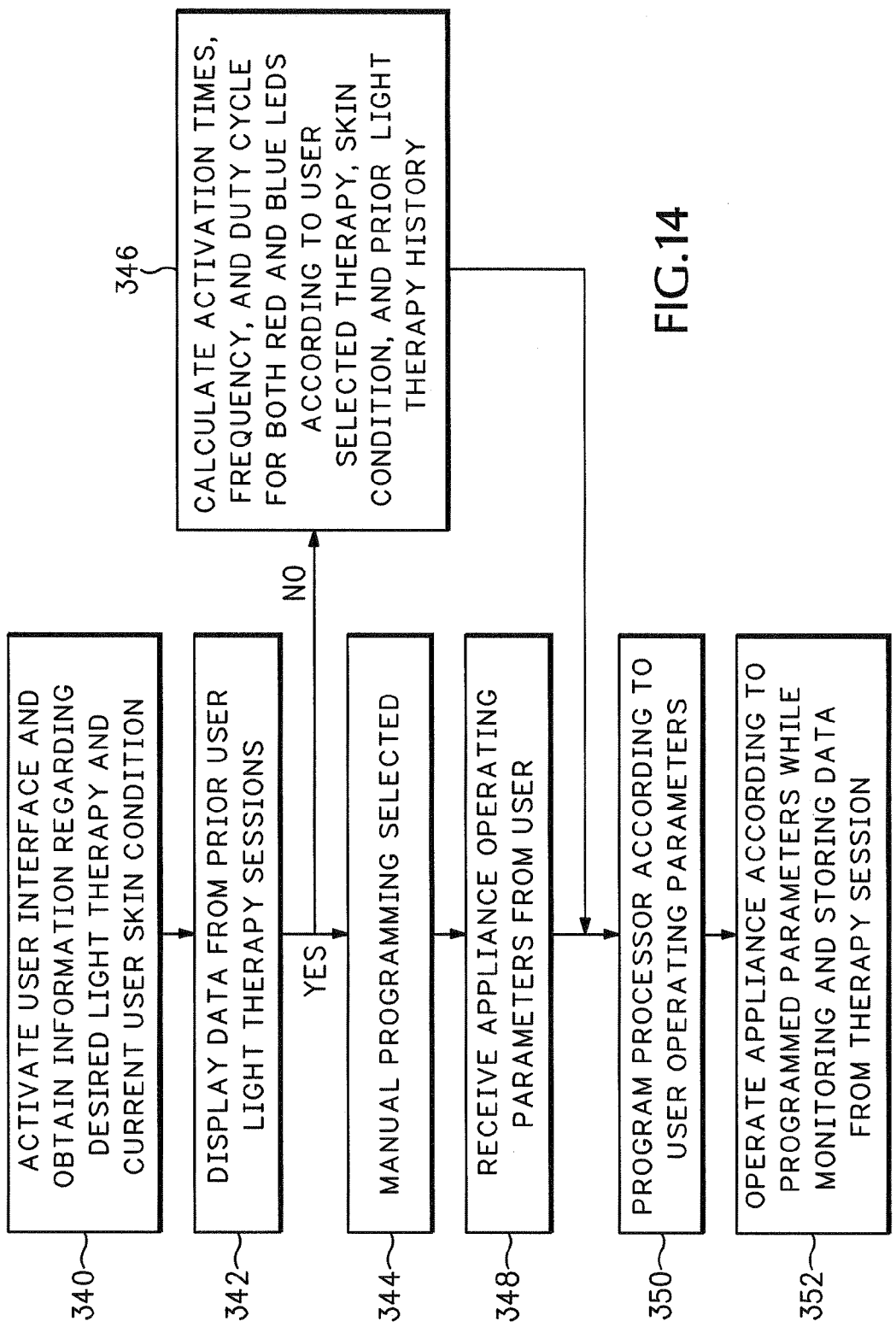

US 8,313,518 B2

SKIN THERAPY SYSTEM

RELATED APPLICATIONS

This application is a continuation of and claims priority to pending U.S. patent application Ser. No. 11/971,166, filed Jan. 8, 2008, entitled, SKIN THERAPY SYSTEM, all of which is incorporated herein in its entirety.

This application is related to U.S. patent application Ser. No. 11/971,134, filed Jan. 8, 2008, entitled, SKIN THERAPY SYSTEM, now abandoned.

TECHNICAL FIELD

The present disclosure relates generally to appliances and/or topical ointments used for skin therapy.

BACKGROUND

Light Emitting Diodes (LEDs) and lasers have been used for skin therapy, such as for treating acne and for reducing wrinkles Most existing light therapy devices are large expensive devices that are located in salons or in doctor's offices. The face of a patient is located next to a machine that then radiates powerful laser or LED light. Many of these light therapy machines burn a top layer of skin off the patient. The patient then re-grows a new skin layer that is healthier and may contain fewer wrinkles than the previously removed skin layer. These stand-alone light therapy devices are too expensive for patient purchase and are not intended for frequent periodic use. For example, a patient's skin would be severely burn and could be permanently damaged if this high intensity laser was applied to the skin every day.

Other hand-held light therapy devices exist. Some of these devices contain LEDs that are activated and directed toward the skin of the user. However, none of these hand-held devices have been proven to be very effective in the treatment of skin conditions, such as acne and wrinkles. For example, the low light intensity and wave-lengths used in these devices do not appear to be very effective in killing the bacteria that causes acne, stimulating the natural healing process of skin infected with acne blemishes, or reducing wrinkles. Further, all of these handheld devices need to be plugged into a wall socket during operation and therefore are not completely portable. Thus, current hand-held light therapy devices do not appear to provide substantial therapeutic benefit.

BRIEF DESCRIPTION OF THE DRAWINGS

FIG. 11 is a timing diagram showing different operating parameters that may be controlled by the circuitry shown in FIGS. 10A and 10B.

FIG. 14 is a flow diagram showing how the light therapy appliance can be manually or automatically programmed according to either different skin conditions or according to previous light therapy sessions.

INTRODUCTION

Light from Light Emitting Diodes (LEDs) has therapeutic effects when applied to skin. Blue LED light has a wavelength of around 475 nm nanometers (nm) and red LED light has a wavelength of around 650. The shorter blue wavelength has more effect on the top skin layers and has been determined to kill the bacteria that causes acne. Longer red wavelengths tend to penetrate the deeper layers of the skin and have more of a regenerative effect on the skin.

When used together, the blue LED light can be used to kill bacteria and the effects of acne while the red LED light can be used to then regenerate the skin and reduce the recovery time after the acne treatment. The system described below can be used for removing acne but can also be used for other skin therapies. For example, the light therapy system can be used to reduce the effects of aging and wrinkles and can generally be used for revitalizing the condition of skin.

Using light therapy for removing acne, wrinkles, and generally improving the health and look of skin is a repetitive process. For example, LED light is applied to the skin several times a day over the duration of multiple consecutive days. One challenge with light therapy treatment, and especially home light therapy treatment, is that the light therapy sessions are not performed correctly or are performed erratically or inconsistently.

Results from light therapy have at best been mixed due to the light therapy sessions being too cumbersome, too long, or too difficult to correctly perform. Even when a user religiously uses the light therapy device, inconsistencies or inadequacies in the light energy output by the light therapy device can still prevent satisfactory results.

Figure 1:
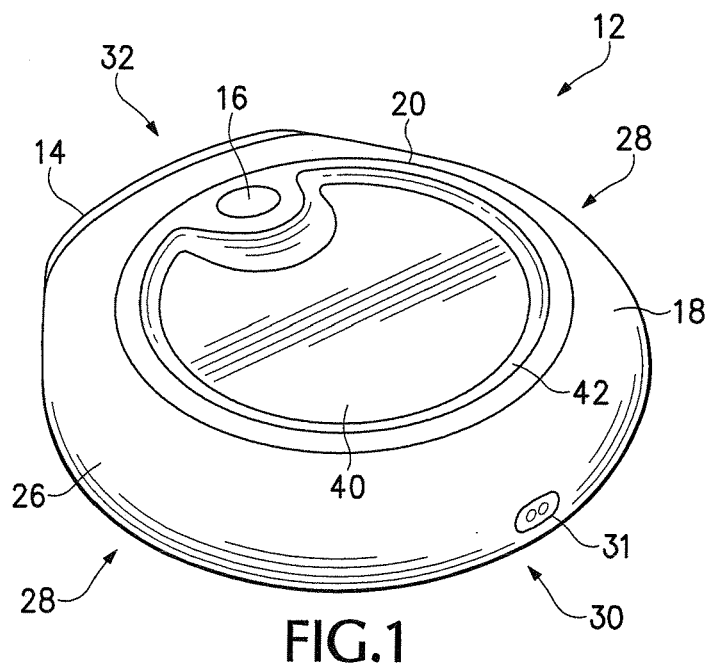
FIG. 1 is perspective view of a light therapy appliance.

FIG. 1 shows a relatively inexpensive light therapy appliance 12 that reduces the complexity and time required for users to perform light therapy sessions while at the same time providing higher performance and more consistent light therapy treatment. Thus, the appliance 12 treats acne, removes wrinkles, and revitalizes skin more effectively than existing hand-held devices.

DETAILED DESCRIPTION

Mechanics and Optics

Figure 2:
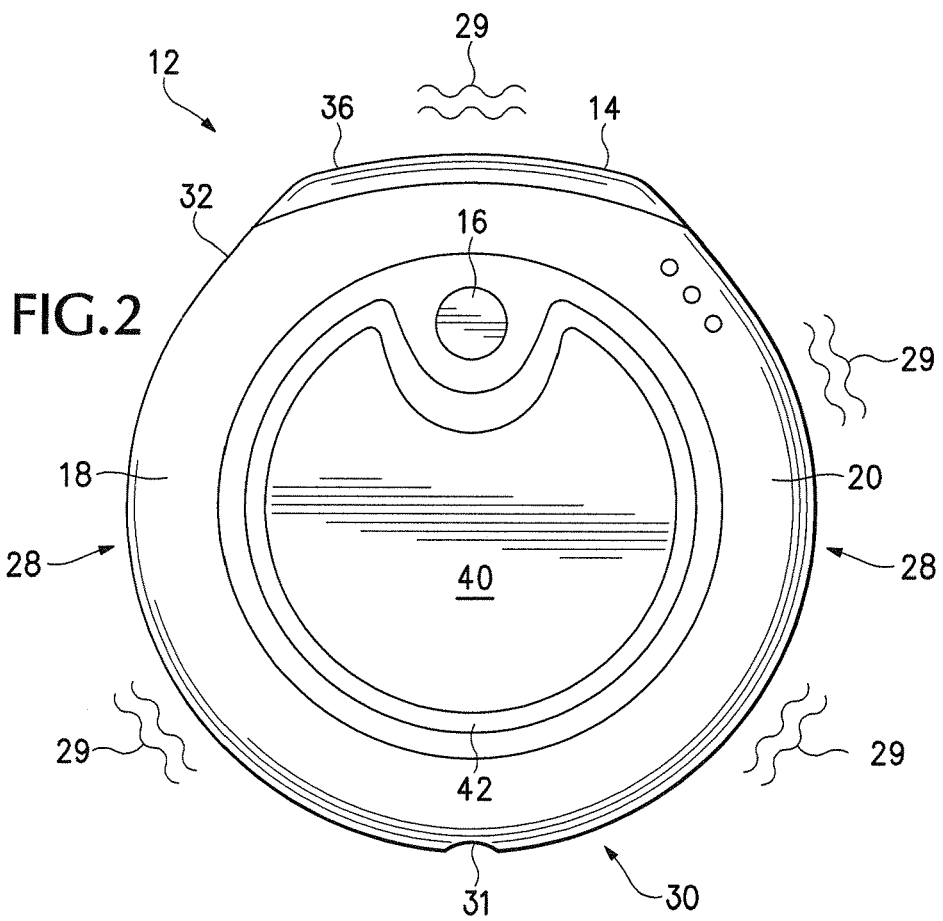
FIG. 2 is a top view of the light therapy appliance in FIG. 1.
Figure 3:
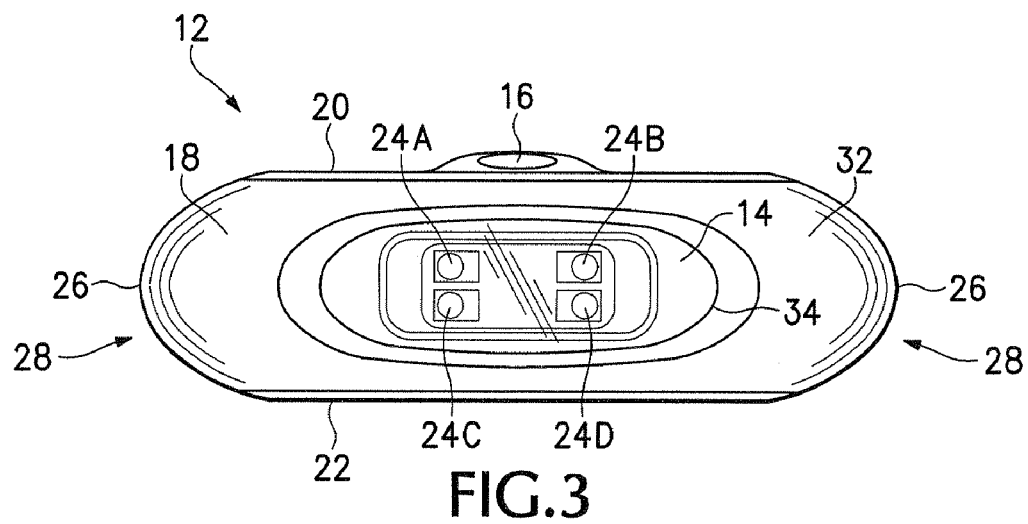
FIG. 3 is a front view of the light therapy appliance.
Figure 4:
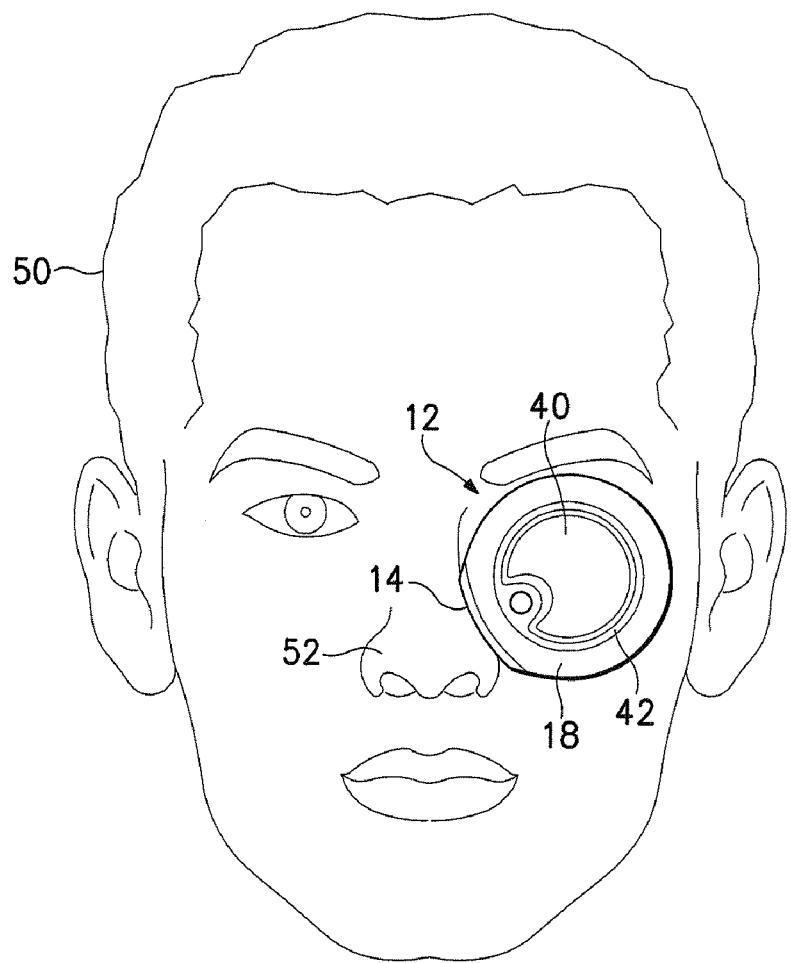
FIG. 4 is view of the light therapy appliance applying light therapy to a user.

FIG. 1 is a rear perspective view, FIG. 2 is a top view, and FIG. 3 is a front elevation view of a hand-held, portable, battery powered light therapy appliance 12. The appliance 12 uses a combination of red and blue light emitted from Light Emitting Diodes (LEDs) 24 to provide improved light therapy treatment for acne and for general skin care.

A hand held enclosure 18 contains an electronic circuit (see FIGS. 10A and 10B) that operate multiple different colored Light Emitting Diodes (LEDs) 24 that emit light at multiple different associated light wavelengths. The enclosure 18 has a substantially disc shape with top and bottom surfaces 20 and 22 with substantially flat circular or oval shapes. A round outer edge 26 extends around the lateral sides 28 and back end 30 of enclosure 18 between the top surface 20 and the bottom surface 22. A socket 31 at the back end 30 is used for recharging a rechargeable battery located inside of enclosure 18.

A grip section 40 extends down into the top surface 20 of enclosure 18 and has a circular or oval shape that is substantially co-centric with the circular oval shape of top and bottom surfaces 20 and 22. The grip section 40 forms a circular ridge 42. An outer edge of enclosure 18 extends around the circular ridge 42. A button 16 activates the appliance 12.

A front clear or translucent lens 14 is attached to a front end 32 of the enclosure 18 and directs the different colored light emitted from the LEDs 24 toward the skin of a user. The lens 14 has a substantially rounded, oval, convex and domed front face 36 that extends between the lateral sides 28 of the enclosure 18. The enclosure 18 and lens 14 form a substantially continuous rounded front end 32. In one embodiment, the enclosure 18 has a diameter of around 78 millimeters (mm) between opposite lateral sides 28 and has a length from the front face 36 of lens 14 to the back end 30 of approximately 79 mm The thickness of enclosure 18 is around 23 mms from top side 20 to the bottom side 22.

In one embodiment, the appliance 12 vibrates 29 whenever the LEDs 24 are in operation. This provides feedback to the user indicating that a light therapy session is being performed. The vibration 29 may also provide a slight stimulation on the skin that informs the user where light therapy has already been applied.

Referring to FIGS. 1-4, the shape of enclosure 18 in combination with the shape of lens 14 are configured to be easier to hold and use and more aesthetically pleasing than existing hand-held light therapy devices. The round disc shape of enclosure 18 allows the appliance 12 to be gripped and manipulated at almost any location by the hand of a user 50 while the user is applying the light from appliance 12 to the skin. The grip section 40 and the formed ridge 42 further allow the user 50 to better grip the enclosure 18 from the front, back, or sides.

The novel curved shape of the front lens 14 allows the appliance 12 to be more easily pressed up against different contours on the face of user 50. For example, acne often appears on the sides and underneath the nose 52. Some of these areas are difficult to access. For example, a light therapy apparatus with a substantially flat front face would not completely fit against the different contoured regions around the nose of user 50.

The rounded domed shape of lens 14 allows a larger working area of the lens 14 to be directly pressed up against irregular face contours of user 50. At the same time, the shape of lens 14, in combination with other reflective and light emittance features of the appliance 12 as described below, radiate a larger amount of more evenly distributed light energy onto these small difficult to access areas on the user 50. Thus, less time is required to provide more effective light therapy.

Figure 5:
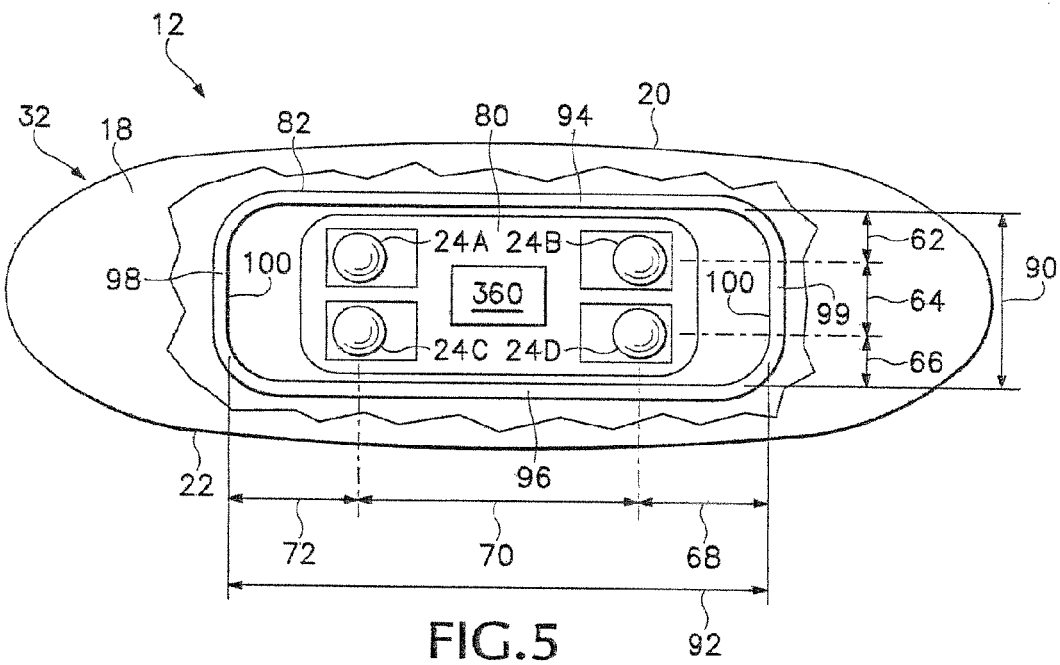
FIG. 5 is front cut-away view of the light therapy appliance.
Figure 6:
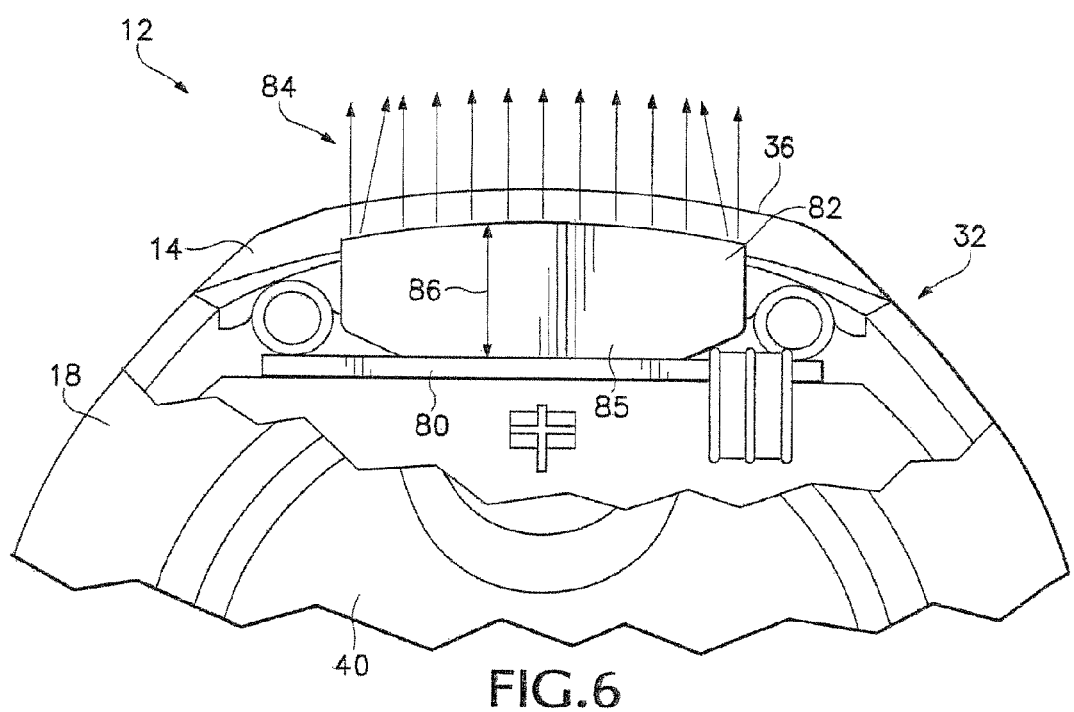
FIG. 6 is top cut-away view of the light therapy appliance.

FIG. 5 shows a front cut-way view and FIG. 6 shows a top cut-away view for the front end 32 of appliance 12. A vertically aligned printed circuit board 80 holds LEDs 24. In one embodiment, a first pair of LEDs 24A and 24D are located in a first pair of opposite diagonal corners of circuit board 80 and each emit a same first color. For example, LEDs 24A and 24D may be red LEDs. A second pair of LEDs 24B and 24C are located in a second different pair of opposite diagonal corners of circuit board 80 and are configured to emit a same second color different from the first color. For example, the second set of LEDs 24B and 24C may be blue LEDs.

Of course it is possible that the first pair of LEDs 24A and 24D may be blue and the second pair of LEDs 24B and 24C could be red. In other embodiments, colors other than red and/or blue could be used. In still other embodiments, all of the LEDs 24 may be the same color or the LEDs 24 could be arranged in different patterns than the rectangular pattern shown in FIG. 5.

The LEDs 24A and 24C are located on a first lateral side of the circuit board 80 and are spaced a distance 70 of approximately 14 mm from LEDs 24B and 24D that are located on a second opposite lateral side of the circuit board 80. The LEDs 24A and 24B are located on a top side of the circuit board 80 a distance 64 of approximately 4 millimeters from the LEDs 24C and 24D that are located on a bottom side of the circuit board 80.

A tubular sleeve 82 has a rectangular cross-sectional shape and surrounds all four LEDs 24. In one embodiment, the sleeve 82 has a length 86 of approximately 9-15 mm, a width 92 of approximately 27-28 mm, and a height 90 of approximately 9-10 mm. The sleeve 82 extends from the circuit board 80 toward the back end of lens 14 so that substantially all of the light emitted from all of the LEDs 24 is directed out a front end of lens 14 as evenly distributed light 84.

The sleeve 82 has a top wall 94 located a distance 62 of approximately 3 mm above the LEDs 24A and 24B and a bottom wall 96 located a distance 66 of approximately 3 millimeters below the LEDs 24C and 24D. A first side wall 98 is located a distance 72 of approximately 6 mm outside and to the left of LEDs 24A and 24C and a second side wall 99 is located a distance 68 of approximately 6 mm outside and to the right of the LEDs 24B and 24D.

The sleeve 82 may be formed from injection molded plastic and have a highly reflective aluminum plated or highly polished mirrored inside surface 100 that reflects the multiple different colored light emitted from the LEDs 24. The configuration of the LEDs 24 in conjunction with their positions inside of reflective sleeve 82 causes substantially all of the light emitted from the LEDs 24 to be directed out the front end 82 of sleeve 82 and through the lens 14. This has a substantial advantage of utilizing and directing most of the light energy from LEDs 24 toward the front working surface 36 of lens 14.

It has been discovered that locating the red LEDs 24A and 24D in opposite corners and locating the blue LEDs 24B and 24C in the opposing two opposite corners creates a more even distribution of red and blue light energy from the lens 14. It has further been discovered that using the rectangular arrangement of LEDs 24 in combination with sleeve 82 further increases the overall light energy output from lens 14 while more evenly distributing light energy through the entire front working surface 36 of lens 14.

Figure 7:
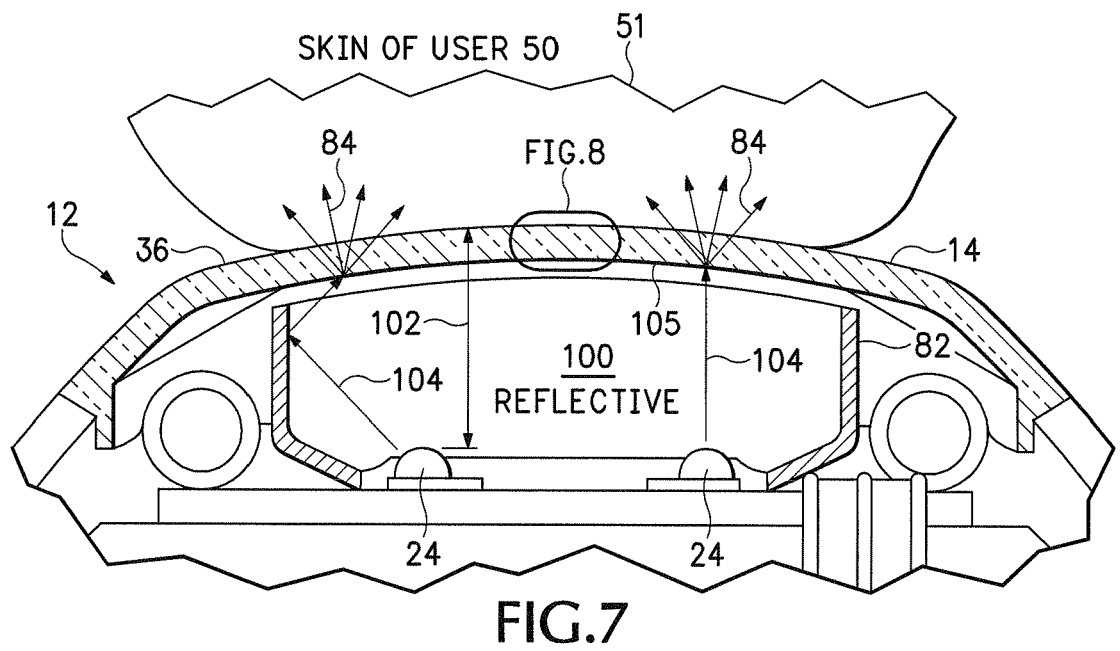
FIG. 7 is a top sectional view of a lens and sleeve used in the light therapy appliance.

FIG. 7 shows a top-sectional view of the sleeve 82 and lens 14. FIG. 7 also shows the light therapy appliance 12 pressed directly up against the skin 51 of user 50 previously shown in FIG. 4. A particular range of distances 102 between the LEDs 24 and the lens 14 provide improved light collation and a substantially uniform distribution of light energy across the front surface 36 of lens 14. In one embodiment the distance 102 from the LEDs 24 to the front face 36 of lens 14 is approximately 13 mm. However, distances 102 in a range of between 10-16 mm still provide substantially even light distribution across the front face 36 of lens 14.

Locating the LEDs farther distances 102 from the lens 14 may provide more even energy distribution out the front side of lens 14. However, placing the LEDs 24 too far from the lens 14 may cause light energy loss. Thus, the distance range of 10-16 mm provides both even energy distribution while also allowing a substantial amount of light energy from LEDs 24 to be emitted from the front face of lens 14. In one embodiment, a distance range of 12-15 mm was shown to be optimal for even energy distribution and maintaining high light energy intensity.

In one embodiment, the lens 14 of appliance 12 is designed to be pressed directly against the skin 51 of the user 50 while the LEDs 24 are emitting light 84. To promote this direct contact, the lens 14 in one embodiment is made from a medical grade plastic such as a Class VI acrylic, styrene methyl methacrylate copolymer manufactured by Ineos Nova or a UV stabilized co-polyester. The class VI medical copolymer is an optical grade that allows the lens 14 to be pressed up against the skin 51 without infecting or irritating open acne pustules. A similar acrylic, styrene methyl methacrylate copolymer material may be used to form the sleeve 82 such that a highly polished inside surface of the copolymer reflects the light 104 from LEDs 24 out through lens 14. Using a highly polished plastic could then eliminate having to use a reflective metal plating on the inside surface 100 of sleeve 82.

Other hand held light therapy devices require the user to hover the lens of the device some distance above the top of the skin 51. This is likely to result in non-uniform application of light energy. Since these other devices are held above the skin, light energy is also allowed to disperse out from the front of the device into the atmosphere away from the skin 51 of the user.

As can be seen in FIG. 7, the sleeve 82 extends from the LEDs 24 to a back side 105 of lens 14 and directs substantially all of the light 104 emitted from the LEDs 24 directly into the skin 51. Locating the LEDs 24 a precise distance 102 from the front surface of lens 14, in combination with using the sleeve 82 to funnel all light from LEDs 24 out of lens 14 while also allowing the appliance 12 to be pressed directly against the skin 51 during operation, allow the user 50 to self-apply more uniform and consistent light energy 84 to the skin.

Figure 8:
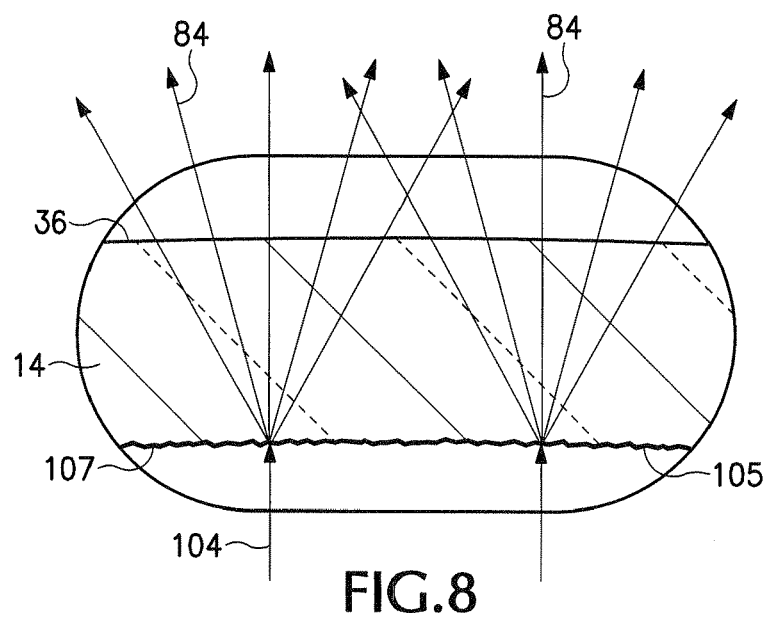
FIG. 8 is an enlarged cross-sectional view of a portion of the lens shown in FIG. 7.

FIG. 8 shows an enlarged sectional view of the lens 14. To further promote a more uniform distribution of light energy 84 onto the skin 51, the lens 14 may include a textured back surface 105 and smooth front surface 36. The textured back surface 105 diffuses the light 104 initially emitted from the LEDs 24 and the diffused light 84 is more evenly distributed across the entire front working side 36 of lens 14. This eliminates "dead-zones" on the front side 36 of the lens 14 that have lesser amounts of light energy. Protuberances 107 on the textured back side 105 of lens 14 in one example may be approximately 0.025-0.100 mm high and may have a variety of different random shapes that are formed into the back surface 105 using a hot press operation during the forming of lens 14.

Figure 9:
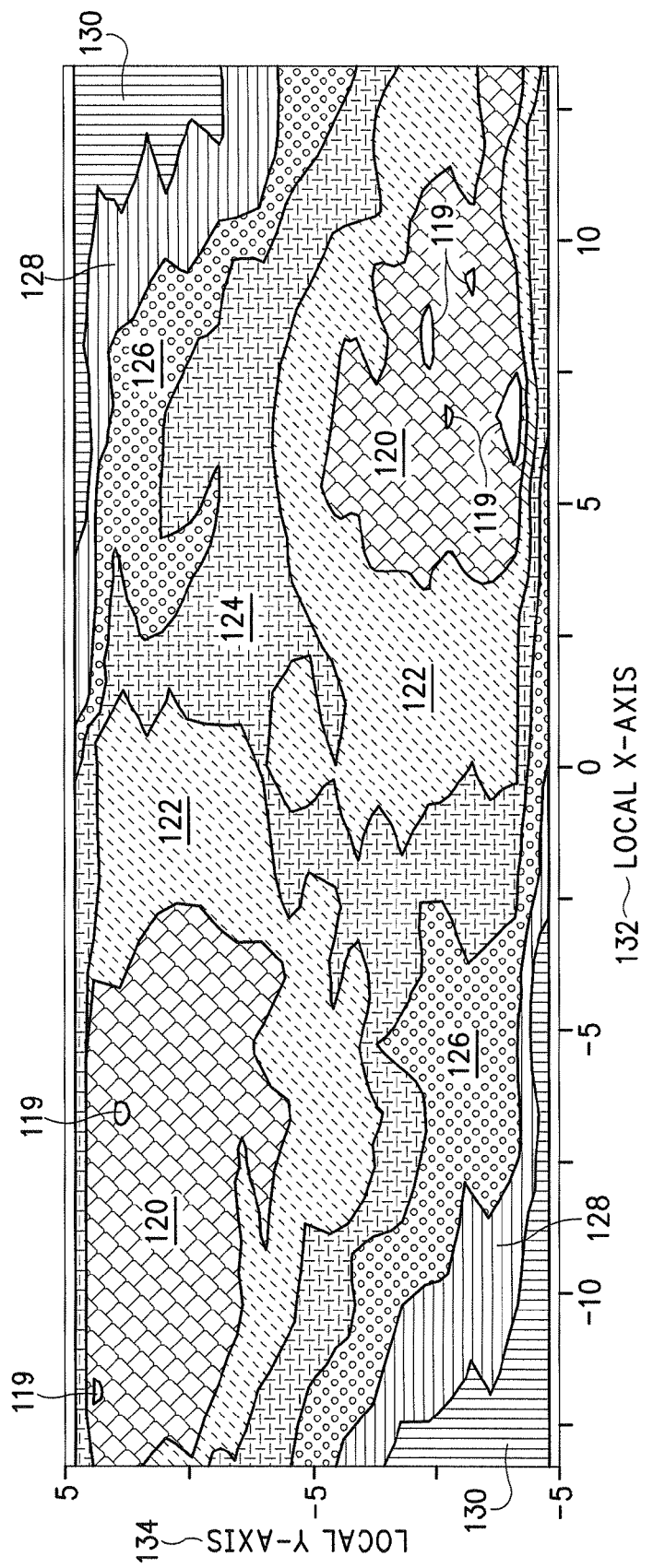
FIG. 9 is a light intensity graph for light coming out of the lens shown in FIG. 7.

FIG. 9 shows the distribution of light energy output from the red LEDs 24A and 24D (FIG. 5) at different x-y locations on the front face 36 of lens 14.

| Region | Light Energy (Watts/mm$^2$) |
| --- | --- |
| 119 | 189-203 |
| 120 | 175-189 |
| 122 | 161-175 |
| 124 | 147-161 |
| 126 | 133-147 |
| 128 | 119-133 |
| 130 | 104-119 |

The x-axis 132 in FIG. 9 represents the horizontal axis of the front face 36 of lens 14. The 0 x-axis value is at the vertical centerline of lens 14 and the +/−5 and 10 increments to either side of the 0 value are in millimeters. The y-axis 134 represents the y-axis of the front face 36 of the lens 14. The vertical 0 y-axis value is the horizontal centerline of lens 14 and the +/−5 increments above and below the 0 value are in millimeters.

It can be seen that the light energy levels represented by the regions 120-130 are all distributed relatively evenly throughout the entire front surface 36 of lens 14. This even light energy distribution results in more controllable and effective light therapy when the light 84 is applied to the skin 51. Also notice that the higher light energy levels are directed in the middle of the lens 14 and then only slightly reduce towards the outsider corners of the lens 14.

Without this even light energy distribution, different amounts of light energy would be output at different lens locations. This could possibly create or prevent therapeutic benefit to some skins areas and create unreliable light therapy results. In the system described above, substantially all of the light energy 84 is output evenly throughout the entire working surface 36 of the lens 14. Thus, applying any location of the lens 14 to any skin area should provide substantially the same therapeutic effect.

The even distribution of light energy as shown in FIG. 9 is a result of one or more of the reflective sleeve 82 surrounding and directing substantially all of the light 104 (FIG. 7) from the LEDs 24 out through the lens 14, the relative position of the LEDs 24 from each other and their relative position inside of sleeve 82, the particular range of distances 102 the LEDs 24 are located from the front surface 36 of the lens 14, the light diffusion created by the textured inside surface 105 of lens 14, and the particular amount of light energy output from the LEDs 24.

Electronics

Figure 10A:
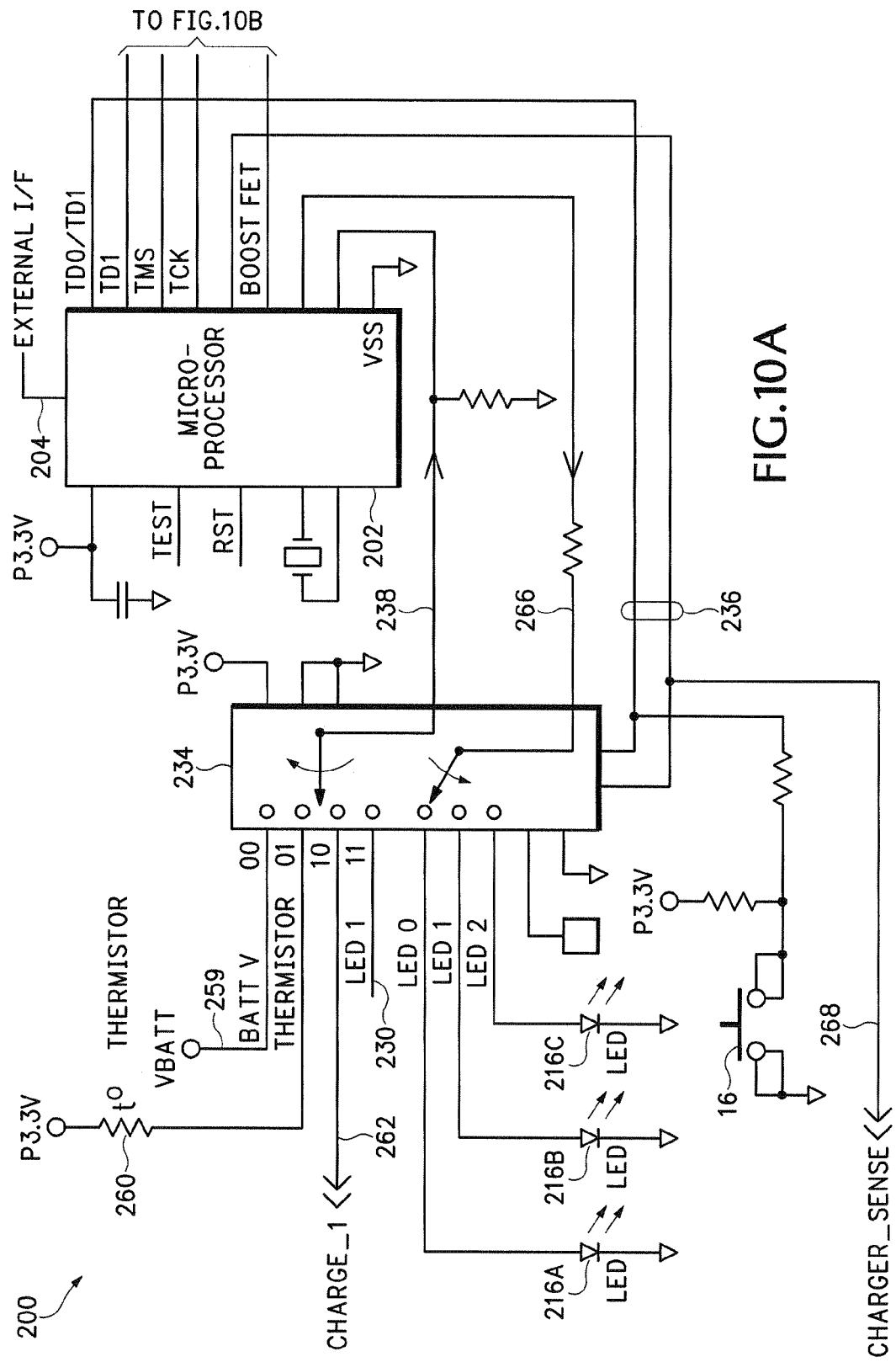
FIGS. 10A and 10C are a circuit diagram for circuitry contained within the light therapy appliance.
Figure 10B:
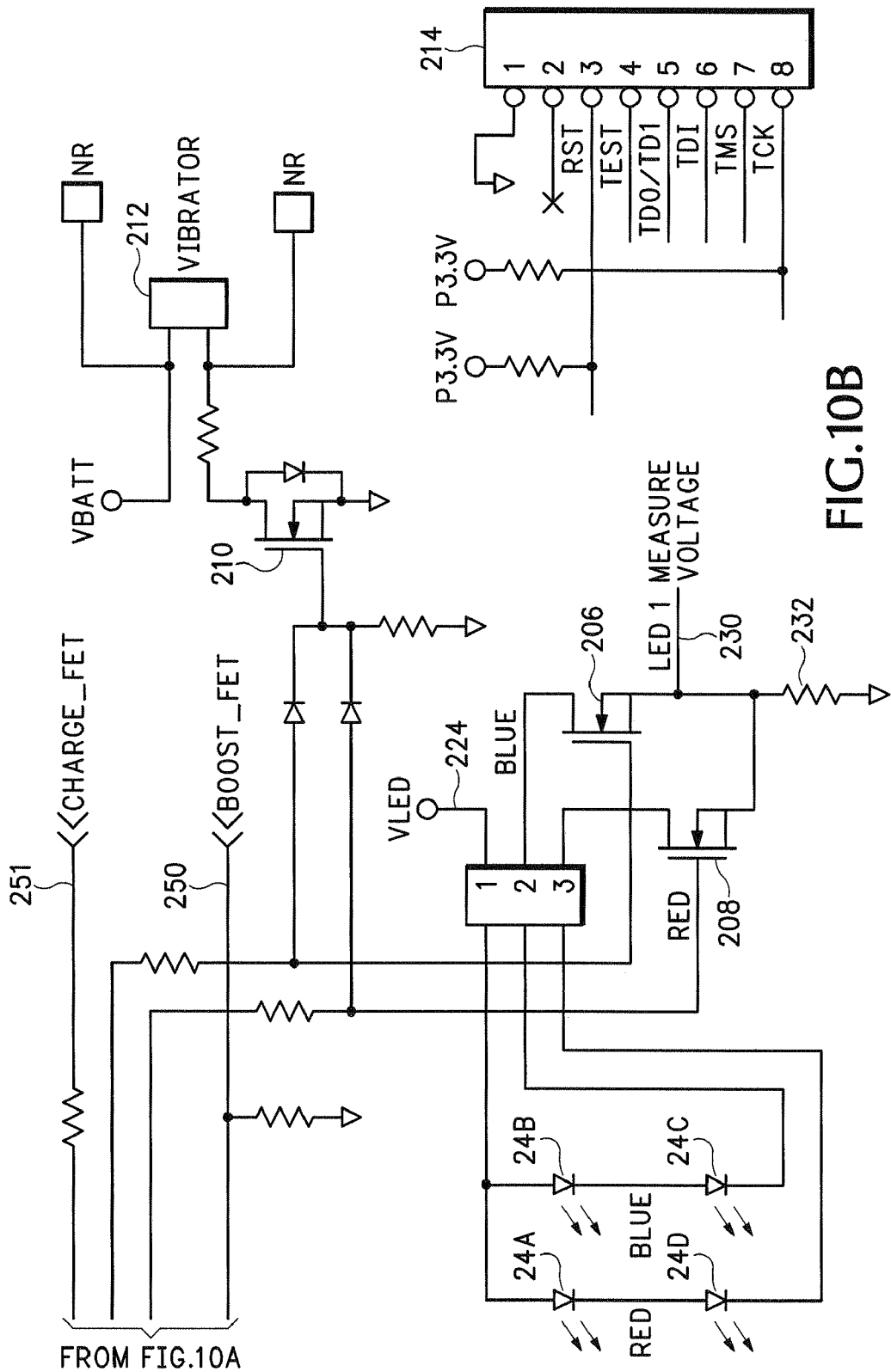
Figure 10C:
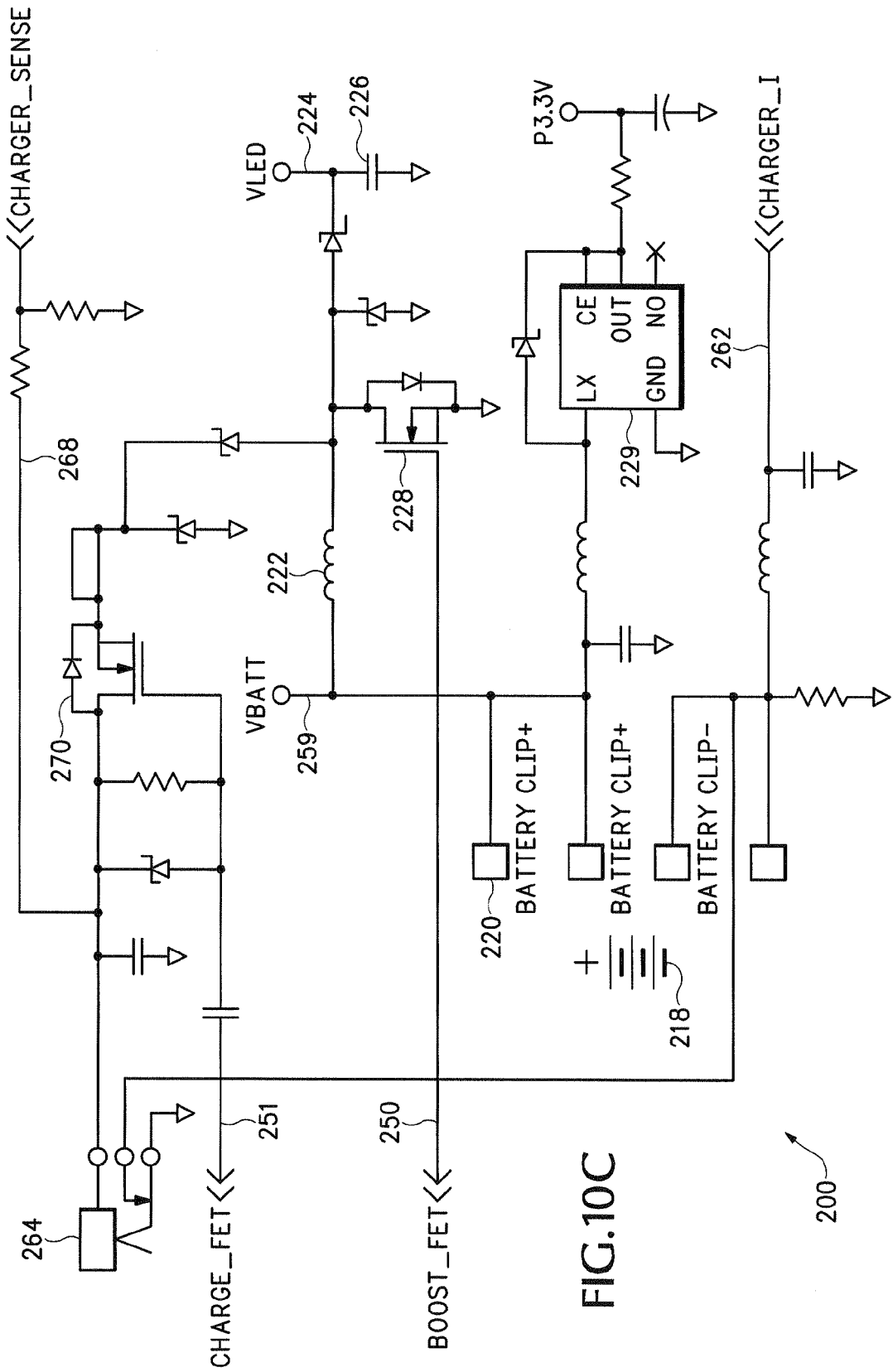

FIGS. 10A and 10C show circuitry 200 used inside of the appliance 12 of FIG. 1. A programmable micro-processor 202 is used for controlling the different operations described below. A port 214, or a different serial or parallel port 204, can be used for accessing internal signaling in the circuit 200 and communicating with or programming processor 202.

A rechargeable battery 218 is inserted into battery clips 220 and the LEDs 216A-216C indicate an amount of charge in battery 218. In one embodiment, the battery 218 is a rechargeable AA nickel metal hydride battery with a voltage of around 1.2 to 0.9 volts. The voltage regulator 229 provides a reference for measurements performed by the processor 202 when boosting the voltage up to 3.3 volts.

The processor 202 contains internal memory that stores instructions that are then executed to provide different light therapy operations. The processor 202 not only turns on the red LEDs 24A and 24D and the blue LEDs 24B and 24C, but also programmably controls how long each LED 24 is turned on, and in alternative embodiments can programmably control the duty cycle used for powering the LEDs 24. In another embodiment, the LEDs 24 can be pulsed or driven at a constant current under software control by the processor 202. The processor 202 can also track the number of therapy sessions previously performed by a user, when and how long the user activated the different red and blue LEDs, and the amount of blue and red light energy output during the different light therapy sessions. This information can be used to either manually or programmably customize light therapy sessions for individual users.

A Field Effect Transistor (FET) 206 is turned on by the processor 202 to activate the blue LEDs 24B and 24C and a FET 208 is turned on by the processor 202 to activate the red LEDs 24A and 24D. Whenever, FET 206 or FET 208 is turned on, a FET 210 is also turned on activating a vibrator 212. As described above in FIG. 2, the vibrator 212 creates a vibration 29 in the appliance 12 that provides feedback notifying the user that at least one pair if LEDs 24 are activated and the light therapy session is in progress.

The LEDs 24 are novel in their use for light therapy and provide more light energy than would typically be available in a handheld battery powered light therapy appliance. The blue LEDs 24B and 24C in one example are manufactured by Luxeon, Rebel, royal blue, LXML-PR01-175 and have a wavelength of 455 nano-meters (nm), operating voltage of 6.2 volts (with 2 each in series), operating current of 120 mA optical power of 85 milliWatts/cm$^2$ which as installed in the device creates an energy density of 15.3 J/cm$^2$ or 0.25 J/cm$^2$.

In one embodiment, the red LEDs 24A and 24D are Luxeon, Rebel, red LXML-PD01-0030, have a wavelength of 632 nm with a LED wavelength range is 620-645 nm, operating voltage of 5.06 volts (with 2 each in series), current 164 mA, optical power of 104 mW/cm$^2$, and energy density of 31.2 J/cm$^2$ or 0.5 J/cm$^2$. The first energy density value assumes a 5 min (300 seconds) exposure, dwelling at one location and the second energy density value assumes the appliance 12 is slowly moving across half the face surface area (175 cm$^2$) for 300 seconds.

The energy density values may change or be programmed by an operator according to the user skin type or according to any other desired therapeutic effect or skin condition. The LEDs 24 described above provide substantial light energy that improve the light therapy results, however other types of LEDs 24 can also be used.

Optimal operating values for the LEDs 24 at node 224 include a voltage of around 6 volts and a current of around 160 mA. In order to increase the voltage from battery 218 to 6 volts, the processor 202 first charges up inductor 222 by turning on FET 228. When the FET 228 is turned off, the current stored in inductor 222 rapidly discharges into capacitor 226 and whichever LEDs 24 are activated by FETs 206 and/or 208. The capacitor 226 maintains a relatively constant voltage at terminal 224 during the discharge of inductor 222.

A sensing signal 230 at the top of resistor 232 determines how much power is being applied to the LEDs 24 through the inductor 222. The processor 202 generates control signals 236 that determine what inputs from mux 234 are directed back to processor 202 on line 238. The processor 202 at one stage programs lines 236 so that sensing signal 230 is fedback on line 238 to an analog-to-digital input on processor 202.

The processor 202 compares the power level associated with the voltage on sensing signal 230 with a programmable target power threshold. When either pair of FETs 24A and 24D, or 24B and 24C, are activated, the processor 202 measures voltage on line 230. The processor 202 then dynamically adjusts the amount of charge provided to inductor 222 according to the measured voltage on line 230.

For example, the voltage across resistor 232 may be above a predetermined voltage threshold if the inductor 222 generates a current through resistor 232 above 160 mAs. The processor 202 detects this high voltage value on line 238 and accordingly during a next operating stage reduces the charge times for inductor 222. If the current through resistor 232 is determined to be some amount less than 160 mAs, the voltage on sense line 230 will be below a predetermined low threshold value. Accordingly, the processor 202 during a next operating stage increases the charge times for the inductor 222.

Referring to FIGS. 10 and 11, the processor 202 operates as a Pulse Width Modulator (PWM) generating a pulse wave signal 250 (BOOST_FET) with a programmable frequency 252 (period T) and a programmable duty cycle duration 254. The inductor 222 in FIG. 10B is charged by battery 218 during the active duty cycle 254A and discharged into the LEDs 24 during time 255A in period 252A. During the discharge period 255A, signal 250 goes low shutting off FET 228 and causing the charge in inductor 222 to activate the enabled LEDs 24 and charge capacitor 226.

The processor 202 measures the sense signal 230 after some number of these charge/discharge cycles 252. For example, the processor 202 may measure the sense signal 230 every 8 milliseconds. If the current through the LEDs 24 is too low, the duty cycle 254A is increased by one increment to duty cycle 254B and accordingly the discharge period 255A is reduced to duration 255B. Another 8 milliseconds later the processor 202 re-measures the voltage on sense signal 230 and either leaves the duty cycle as is or adjusts the duty cycle 254B according to the new measurement on sense signal 230. For example, if the voltage on sense signal 230 is too high, the duty cycle 254B is decreased by one time increment.

Accordingly, the processor 202 very precisely controls the current to the LEDs 24. The light output of the LEDs is proportional to the current through the LEDs. This relatively large light energy level output from the LEDs 24, as provided by the switching power supply circuit, increases the therapeutic effectiveness of the appliance 12. This large amount of light energy is also generated from a relatively small rechargeable battery 218. Thus, the selective charging and discharging of inductor 222 by processor 202 allows a portable handheld battery operated appliance 12 to provide highly effective light therapy.

Charging of battery 218 is also closely controlled. A voltage signal 259 from battery 218 is monitored by the processor 202. A thermistor 260 is monitored by the processor 202 to determine the temperature of battery 218 and to prevent charging the battery 218 when the battery temperature is either too cold or too hot.

A charge sense signal 268 is monitored by the processor 202 to detect when an external Direct Current (DC) power supply adapter 264 is connected to the appliance 12. When the charge sense signal 268 indicates the power adapter 264 is connected, and a battery charging session is appropriate, the processor 202 activates signal 251 (CHARGE_FET). Activated signal 251 turns on FET 270 allowing power from the power adaptor 264 to charge both the inductor 222 and the battery 218.

The processor 202 monitors the voltage on line 262 to maintain a constant charge current. This is done using the pulse width modulator in the same way as the LED current is maintained. For example, the duty cycle of the signal in FIG. 11 is varied according to the voltage on line 262. The charging cycle is terminated in one of multiple ways: too high of temperature is sensed, rate of temperature rise is exceeded, timer value is exceeded, voltage on the battery exceeds a defined value, or if the battery voltage hits a plateau.

Light Therapy Sessions

The following description provides one example of light therapy sessions used for treating acne. Of course other types of light therapy sessions can also be performed according to the type of skin condition to be treated. Any variety of different topical ointments can be used in conjunction with the light therapy appliance 12. However, it has also been discovered that particular substances listed below are particularly effective in treating acne when used in conjunction with the light therapy provided by appliance 12.

Light Therapy Stage

Once the skin is thoroughly cleaned, the light therapy appliance 12 is turned on and the blue and red light from LEDs 24 is applied to the acne affected skin. The exact activation period of the red and blue LEDs 24 may vary according to the user or according to the current stage of light therapy. For example, the LEDs 24 could be activated for two minutes, five minutes, or ten minutes. Further, the blue LEDs could be turned on for a different amount of time than the red LEDs according to the particular therapy stage of the user. The number of blue and red LEDs that are activated could also vary for different skin conditions or during different treatment stages. In an alternative embodiment, it is also possible to activate both the blue LEDs and the red LEDs at the same time.

In the example below, the blue LEDs are first activated for five minutes and then the red LEDs are activated for five minutes. Pressing button 16 wakes up the processor 202. The processor 202 confirms adequate charge in battery 218 and then activates the appropriate number of fuel LEDs 216 via line 266 and mux 234 to visually indicate an amount of charge remaining in the battery 218.

When sufficient charge exists in battery 218, the processor 202 first slowly turns on the blue LEDs 24B and 24C over a period of around two seconds. At full blue light intensity, the processor 202 begins a countdown from 5 minutes. The vibrator 212 is also activated during the 5 minute operational phase. The fuel LEDs 216 are illuminated by the processor 202 providing feedback to the user about battery level status. The user then places the front side 36 of lens 14 directly on the skin 51 (FIG. 7).

The user 50 applies a slow, sweeping motion, gently running the lens 14 along the skin surface 51 for five minutes until an automatic timer in processor 202 turns off the vibrator 212 and LEDs 24B and 24C. At the end of the five minute session, the blue LEDs 24B and 24C are powered down slowly over two seconds by the processor 202. The blue LEDs are now off and the vibrator 212 pulses two times over two seconds.

The red LEDs 24A and 24D are then slowly powered on by the processor 202 over two seconds. The vibrator 212 starts again at the beginning of the red power up cycle. When the red LEDS 24A and 24D reach full intensity, the unit begins another countdown from five minutes. Of course as mentioned above, the duration of the red or blue LED activation time periods can be reprogrammed to different values.

At the end of the five minute red light session, the vibrator 212 stops and the red LEDs 24A and 24D conduct a two-second fade out, indicating the light therapy session is over. The battery level indicator LEDs 216 continue to illuminate for three seconds, providing feedback informing the user if the battery 218 should be recharged. After three seconds of illumination, the battery level LEDs 216 power down over an additional three seconds, and the appliance 12 completely shuts-off. The user can then press the power button 16 again to initiate another light therapy session.

If the user wishes to initiate a red light session first, the following procedure is conducted. If appliance 12 is off, then the user presses the power button 16 two times to initiate a red light session. Vibrator 212 and battery level LEDs 216 activate immediately. Red LEDs 24A and 24D are powered on by the processor 202 over two seconds, and the red light session begins.

If the appliance 12 is currently in a blue light session, then the user can press the power button 16 once to initiate the red light session. This causes the processor 202 to immediately turn off LEDs 24B and 24C, pulse vibrator 212 twice, and turn on the red LEDs 24A and 24D over two seconds. The red light therapy session then continues for five minutes.

To perform a manual override to shut off appliance 12, the power button 16 is pressed twice anytime during a blue light session or pressed once during a red light session. The vibrator 212 and main light are immediately powered off.

Therapy Characterization and Programming

Figure 12:
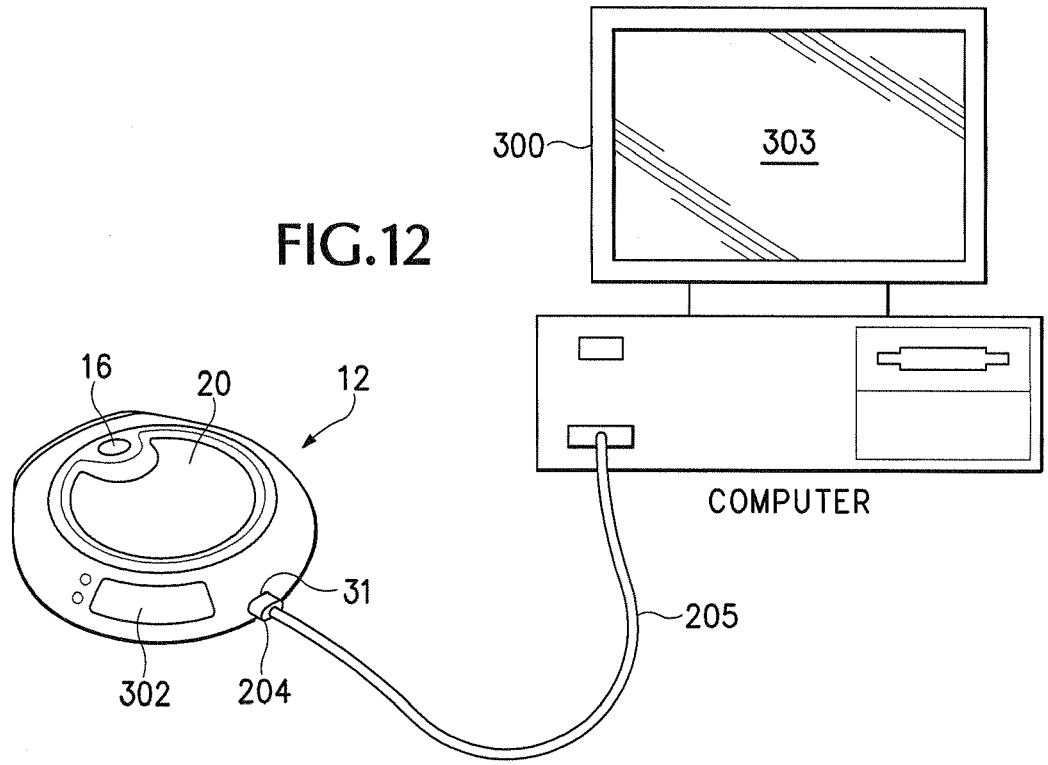
FIG. 12 is a diagram showing how the light therapy appliance can be programmed.

FIG. 12 shows one embodiment where the light therapy appliance 12 is plugged into a Personal Computer (PC) 300. As explained above, the same light therapy treatment may not necessarily work best for all users or for all skin conditions. A user with lighter skin may get better results from a different light therapy regime than the light therapy regime used by someone with darker skin. Other users may have different severities of acne or aging that may also dictate different light therapy processes. Accordingly, either through the computer 300 attached to the external I/O port 204 or through a programmable user interface 302 located directly on the appliance 12, a user, physician, or therapist may program different operating parameters into the circuitry 200 in FIGS. 10A and 10B.

The I/O port 204 may plug into the same socket 31 used for powering the rechargeable battery 218. For example, a Universal Serial Bus (USB) cable 205 may be used for both providing power to battery 218 and also sending and receiving digital data to and from the processor 202. In alternative embodiments, the port 204 may be inserted into a different socket than the power socket 31.

Figure 13:
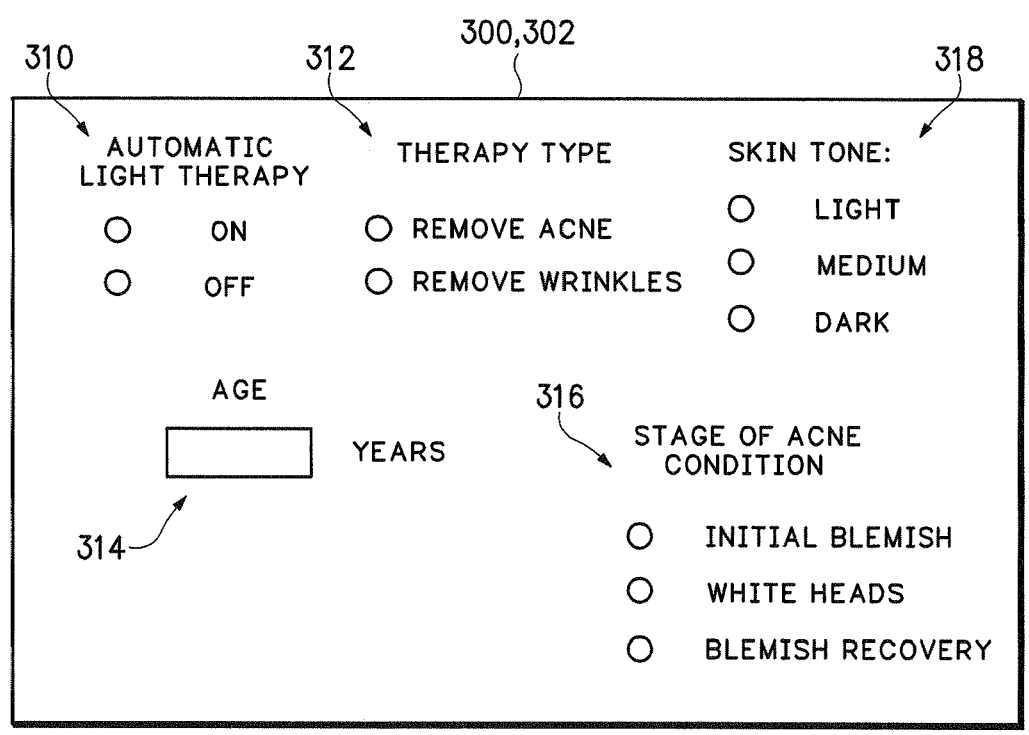
FIG. 13 shows how the light therapy appliance may customize light therapy sessions according to different user skin characteristics.

FIG. 13 shows one embodiment where software operated either in the processor 202 inside of the appliance 12, or operated by PC 300, displays different questions either on interface 302 or screen 303, respectively. Of course these are just examples of some of the many different questions the software may ask the user.

A field 310 may allow the user to enable of disable a customized automatic light therapy session. Field 312 may ask the user to select either light therapy for acne removal or light therapy for wrinkle removal and skin regeneration. A field 318 may ask the user to enter their particular skin tone. If relevant, the age of the user may be entered in field 314. If the user selects light therapy for acne removal, the software may also ask the user if they are currently in an initial, intermediate, or recovering stage of an acne outbreak.

The processor 202 in FIG. 10A may then be programmed to provide a particular type of light therapy directed to the specific inputs entered by the user in FIG. 13. This may involve varying any combination of activation periods for the red LEDs and blue LEDs. The light energy levels and pulsing may also be automatically adjusted according to the type of applicable light therapy. For example, referring back to FIG. 11, the software may program processor 202 to adjust any of the time period (frequency) 252, inductor charge period 254, or inductor discharge period 255. The threshold voltage level compared with voltage sensing signal 230 may also be varied to either increase or decrease the amount of light energy output by the LEDs 24. The number or combination of activated red and blue LEDs may also be varied.

FIG. 14 shows one example of how the software executed either in processor 202 or in PC 300 may automatically customize a light therapy session. In operation 340 the user interface 302 or 303 is activated. The user enters information that identifies the type of desired light therapy and any particular user skin conditions. For example, the user may select light therapy treating an acne condition and may indicate that the acne condition is relatively severe.

In operation 342, the processor 202 or PC 300 may display data from prior light therapy sessions for the user. Recall from the description in FIG. 10 that the processor 202 can monitor and store just about any parameter from prior light therapy sessions. For example, the processor 202 can determine how many light therapy sessions have been performed over the last month.

The processor 202 can also keep track the total light energy applied in each prior session and calculate a total amount of light energy applied to the skin over the last week, month, year, etc. The processor 202 can also track the history of how much red light energy and blue light energy the user has applied to their skin over any particular period of time. This information may be important for a light therapy program that changes LED operating parameters for different light therapy stages.

For example, as explained above, the shorter blue wavelength is initially used to isolate and kill the bacteria on the top layer of the skin that causes acne. The red light penetrates deeper into the skin than the blue light and has the effect of stimulating collagen growth and tissue regeneration. Thus, as acne clears, the user may want to spend less time with the blue LED light and more time with the red LED light.

Accordingly, a user with an early stage of acne may want to apply equal amounts of red and blue LED light to the skin, say for five minutes each, twice a day, and for two weeks. After the two weeks, the light therapy may be automatically changed to two minutes of blue light and six minutes of red light once a day.

The processor 202 can determine when it is time to switch from the first light therapy stage (5 minutes of red light and 5 minutes of blue light) to a second light therapy stage (2 minutes of red light and 6 minutes of blue light). The processor 202 can track and add up all the prior user light therapy sessions and determine when the total amount of red and/or blue light energy applied to the user has reached the second therapy stage.

The processor 202 or PC 300 in operation 342 can then notify the user through user interface 302 or 303 that they have reached the next therapy stage. If the user selects manual operation in operation 344, then the processor 202 can receive user entered parameters in operation 348 for the next and other future light therapy sessions. For example, the user may manually select the amount of time the red and blue LEDs are activated, or select a wave and frequency pattern for signal 250 in FIG. 11. Alternatively, an automatic light therapy session can be disabled and the user can simply manually activate the red and blue LEDs 24 by pressing the power button 16 once or twice as described above.

Alternatively, the processor 202 or PC 300 automatically calculates activation times, frequencies, and duty cycles of both the red and blue LEDs in operation 346 according to any combination of: type of light therapy selected by the user, user personal skin information, and the stored history of the light therapy sessions previously performed by the user.

The processor 202 is programmed in operation 350 to operate according to either the information manually entered by the user in operation 348, the information automatically generated in operation 346, or operate manually by the user simply pressing power button 16. In operation 352, the processor then operates the appliance 12 according the programmed parameters, if any, while at the same time monitoring and storing the light therapy information from the current light therapy session.

In another embodiment, an optical sensor 360 shown in FIG. 5 is coupled to the processor 202 and is used to detect skin protuberances or skin color irregularities that may be associated with acne. The user moves the appliance 12 over the skin and the processor 202 activates the vibrator 212 whenever one of these acne affected areas is detected. This informs the user to keep the appliance 12 over that particular area for a longer period of time.

In yet another embodiment, the sensor 360, or an additional accelerometer, is used to determine if the appliance 12 is moving or in motion. The processor 202 uses the signal from sensor 360, or accelerometer, to identify conditions where the LEDs 24 are activated but the appliance 12 has not moved for some period of time. The processor 202 can then accordingly either turn off the LEDs 24 of reduce the output power of the LEDs 24.

The system described above can use dedicated processor systems, micro controllers, programmable logic devices, or microprocessors that perform some or all of the operations. Some of the operations described above may be implemented in software and other operations may be implemented in hardware.

For the sake of convenience, the operations are described as various interconnected functional blocks or distinct software modules. This is not necessary, however, and there may be cases where these functional blocks or modules are equivalently aggregated into a single logic device, program or operation with unclear boundaries. In any event, the functional blocks and software modules or features of the flexible interface can be implemented by themselves, or in combination with other operations in either hardware or software.

Having described and illustrated the principles of the invention in a preferred embodiment thereof, it should be apparent that the invention may be modified in arrangement and detail without departing from such principles. Claim is made to all modifications and variation coming within the spirit and scope of the following claims.

The invention claimed is:

1. A light therapy appliance, comprising:
   an electronic circuit board retaining one or more Light Emitting Diodes (LEDs) configured to emit light at one or more associated wavelengths, wherein the wavelengths associated with the light are configured to promote at least one of acne removal, wrinkle removal, or skin regeneration;
   a hand held portable enclosure containing the electronic circuit board, wherein the enclosure comprises substantially disc or oval shaped top and bottom walls with rounded sides that extend between a first portion of a perimeter of the top and bottom walls;
   a lens attaching to an opening formed in the enclosure between the top and bottom walls and between the rounded sides along a second portion of the perimeter of the top and bottom walls and configured to direct the light from the LEDs output through the opening formed in the enclosure, wherein a bottom surface of the lens sits substantially flush on a top surface of the opening in the enclosure and the lens forms a substantially continuous contoured outside surface with an outside surface of the enclosure; and
   a sleeve located between the electronic circuit board and the lens and configured to reflect and direct the light emitted from the LEDs out through the opening and through the lens.

2. The light therapy appliance of claim 1 wherein the sleeve comprises elongated top and bottom walls and opposite lateral side walls and the top and bottom walls are longer than the side walls.

3. The light therapy appliance according to claim 2 wherein the sleeve is formed from injection molded plastic and has a reflective aluminum plated, or polished mirrored inside surface, configured to reflect and direct substantially all of the light emitted from the LEDs out through the lens.

4. The light therapy appliance according to claim 2 wherein the sleeve has a substantially rectangular cross-sectional shape.

5. The light therapy appliance according to claim 1 wherein the sleeve comprises a first end with a first opening surrounding the LEDs and a second end with a second opening located proximate to the lens, wherein the second opening is larger than the first opening.

6. A light therapy device, comprising:
Light Emitting Diodes (LEDs) configured to emit light;
a hand held portable enclosure forming an internal cavity for containing the LEDs, wherein the enclosure comprises substantially disc or oval shaped top and bottom walls with rounded side walls extending around a first portion of a circumference of the top and bottom walls, wherein an opening is formed in the enclosure between the top and bottom walls and between the side walls of the enclosure along a second portion of the circumference of the top and bottom walls;
a lens configured to direct the light emitted from the LEDs out through the opening formed in the enclosure, wherein the lens sits on top of the opening formed in the enclosure and forms a substantially continuous contoured outside surface with an outside surface of the enclosure; and
a sleeve located between the LEDs and the lens, and configured to reflect and direct the light emitted from the LEDs out of the opening and through the lens.

7. The light therapy device according to claim 6 wherein the sleeve comprises elongated top and bottom walls and opposite lateral and parallel side walls.

8. The light therapy device according to claim 7 wherein the top and bottom walls are longer than the side walls.

9. The light therapy device according to claim 6 wherein the internal cavity contains both an electronic circuit board for retaining the LEDs and a power supply for powering the LEDs.

10. The light therapy device according to claim 6 wherein the sleeve comprises a first end with a first opening surrounding the LEDs and a second end with a second opening located proximate to the lens, wherein the second opening is larger than the first opening.

11. A light therapy appliance, comprising:
an electronic circuit including Light Emitting Diodes (LEDs) configured to emit light at at least one associated wavelength, wherein the wavelengths associated with the light are configured to promote at least one of acne removal, wrinkle removal, or skin regeneration;
a hand held portable enclosure containing the electronic circuit wherein the enclosure has a substantially disc shape with top and bottom surfaces with substantially circular or oval shapes and a round outer edge that extends around lateral sides and a back end of the enclosure between the top and bottom surfaces;
an opening formed along a perimeter of a front end of the enclosure between the top and bottom surfaces and between the round outer edge that extends between lateral sides of the enclosure, wherein the opening is configured to output the light emitted from the LEDs out from the enclosure; and
a front lens located on top of the opening having a substantially oval outside perimeter and a rounded front convex front face that extends between the top and bottom surfaces and between the lateral sides of the enclosure, the front lens configured to direct the light from the LEDs output through the opening formed along the perimeter of the front end of the enclosure to a top surface of skin.

12. The apparatus according to claim 11 wherein the lens is made from a medical grade plastic configured to be pressed directly against the top surface of skin while the LEDs are emitting different colored light.

13. The apparatus according to claim 11 wherein the lens includes a first substantially smooth front surface for pressing against the skin and a textured back surface configured to diffuse the different colored lights emitted from the LEDs.

14. The apparatus according to claim 11 wherein the LEDs include at least one of the following:
a first pair of LEDs located in a first pair of opposite diagonal corners in the front end of the enclosure and configured to emit a same first color light, and a second pair of LEDs located in a second different pair of opposite diagonal corners in the front end of the enclosure and configured to emit a same second color light different from the first color light;
four LEDs located in opposite diagonal corners in the front end of the enclosure and configured to emit a same color light; or
two LEDs located on a same horizontal line.

15. The apparatus according to claim 14 wherein the first color light is blue and the second color light is red.

16. The apparatus according to claim 11 including a sleeve located between the electronic circuit and the front lens and configured to reflect and direct the light emitted from the LEDs out through the opening and the front lens.

17. The apparatus according to claim 16 wherein the sleeve has a rectangular cross-sectional shape.

18. The apparatus according to claim 16 wherein the sleeve comprises elongated top and bottom walls and opposite lateral and parallel side walls.

19. The apparatus according to claim 18 wherein the top and bottom walls are longer than the side walls.

* * * * *